United States Patent [19]

Kumazawa

[11] 4,015,936
[45] Apr. 5, 1977

[54] METHOD FOR DETERMINATION OF TOTAL NITROGEN AND HEAVY NITROGEN CONTENT

[75] Inventor: Kikuo Kumazawa, Tokyo, Japan
[73] Assignee: Hiryokagaku Kenkyusho, Tokyo, Japan
[22] Filed: Aug. 26, 1975
[21] Appl. No.: 607,799
[52] U.S. Cl. .................. 23/230 PC; 23/232 R; 23/253 PC; 23/254 R
[51] Int. Cl.$^2$ .................. G01N 7/02; G01N 7/18
[58] Field of Search ....... 23/253 PC, 232 R, 254 R, 23/230 PC

[56] References Cited
UNITED STATES PATENTS

| | | | |
|---|---|---|---|
| 3,241,922 | 3/1966 | Walisch | 23/253 PC |
| 3,304,159 | 2/1967 | Hinsvark | 23/230 PC |
| 3,451,779 | 6/1969 | Hozumi | 23/253 PC |
| 3,877,875 | 4/1975 | Jones | 23/253 PC |

OTHER PUBLICATIONS

K. Hozumi et al., Anal. Chem., 35(10), 1522–1527 (1963).
K. Hozumi, Anal. Chem., 38(4), 641–644 (1966).
"Tech. of Org. Chem.", vol. III, A. Weissberger, Ed., 285, 296–298, 303–304, 316, 353, 355, 362–363, Interscience, 1957.

Fisher Modern Laboratory Appliances Catalog 63, p. 960, 1962.

*Primary Examiner*—Morris O. Wolk
*Assistant Examiner*—Sidney Marantz
*Attorney, Agent, or Firm*—Lane, Aitken, Dunner & Ziems

[57] ABSTRACT

The total nitrogen content of a given specimen is determined by sealing the specimen in conjunction with copper oxide and calcium oxide in a tube under vacuum to form a sealed specimen tube, heating the sealed specimen tube and consequently causing the specimen therein to undergo combustion and generate nitrogen, subsequently placing in a vacuumized compartment the resultant sealed specimen tube now containing the generated nitrogen, breaking the tube therein so as to liberate the nitrogen from the tube interior into the compartment and measuring the volume and pressure of the nitrogen thus released in the compartment. The heavy nitrogen content of this specimen is determined by causing a part of the released nitrogen to be collected in a separate tube connected to the compartment in which nitrogen is generated. The tube in which the nitrogen gas is collected is sealed and subsequently the heavy nitrogen concentration in the sealed nitrogen tube is measured by an ordinary method.

1 Claim, 2 Drawing Figures

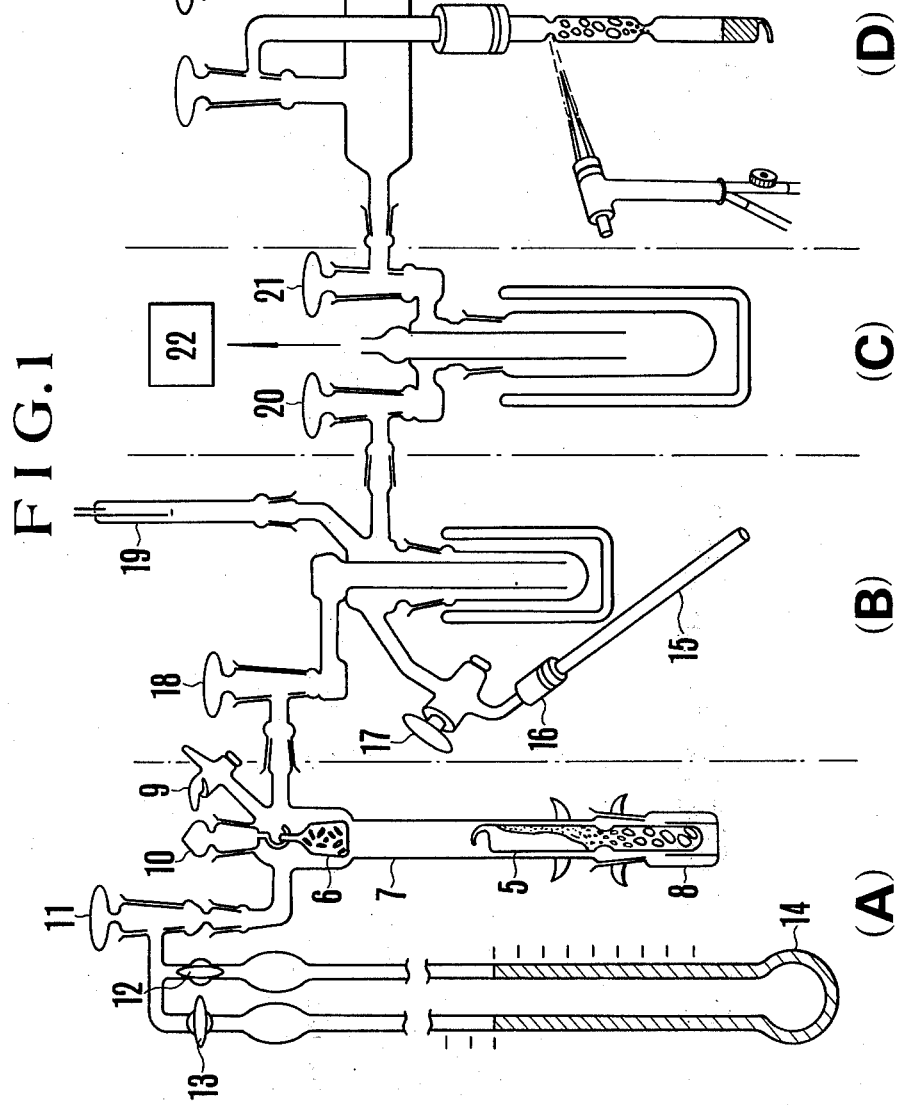

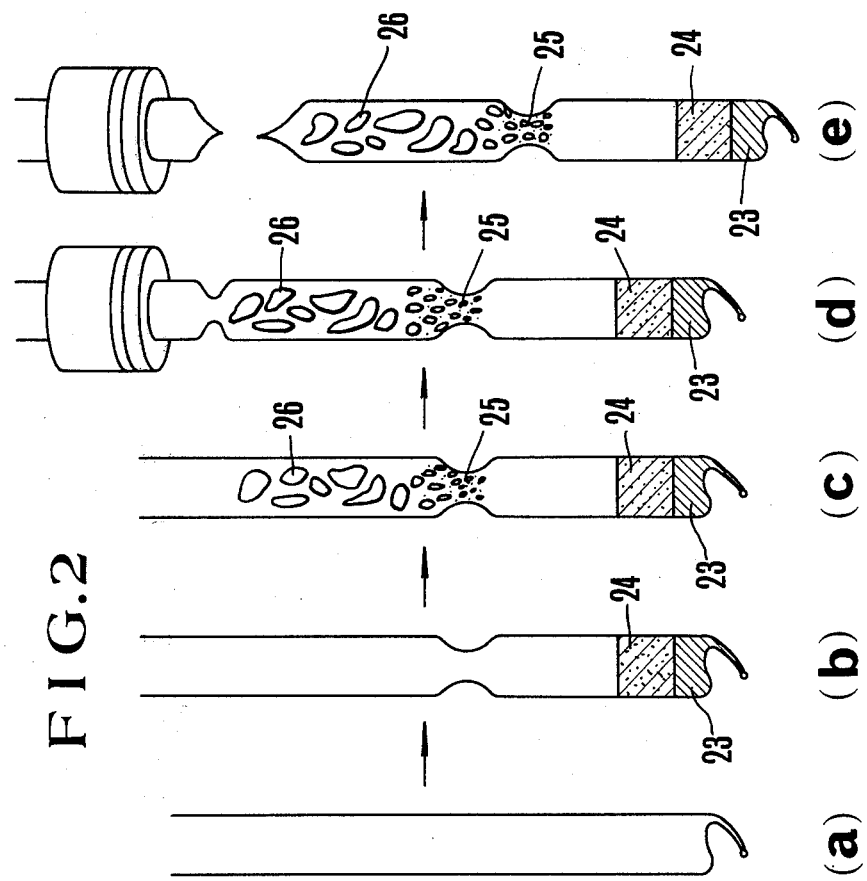

METHOD FOR DETERMINATION OF TOTAL NITROGEN AND HEAVY NITROGEN CONTENT

FIELD OF THE INVENTION

The present invention relates to a method for the determination of the total nitrogen content and the heavy nitrogen content of a specimen which contains both nitrogen ($^{14}N$) and heavy nitrogen ($^{15}N$).

BACKGROUND OF THE INVENTION

For the determination of the heavy nitrogen content of a given specimen, it has been customary to resort to a procedure which involves decomposing the specimen such as by the Kjeldahl method to determine the total nitrogen content of the specimen and thereafter determine the percentage of heavy nitrogen by mass spectrographic or spectroscopic analysis of the portion of nitrogen from the specimen which has been collected in the form of ammonium sulfate. In this procedure, however, when the amount of the specimen used is small, a potential for error in the measurement of the heavy nitrogen concentration is unacceptably increased since the ammonia present in the reagents and in the ambient air enters the reaction system in a relatively large quantity between the time when the specimen is decomposed and the time the nitrogen is recovered in the form of ammonium sulfate.

In recent years, a variety of methods have been developed for the spectroscopic measurement of heavy nitrogen concentration in specimens and analytical devices designed exclusively for such masurement have found widespread acceptance. Even where such a specific analytical device is used, it is necessary that determination of the total nitrogen content of the specimen be made independently and thereafter, determination of heavy nitrogen content of that specimen be effected by measuring the concentration of heavy nitrogen. In the prior art methods described above the determination of total nitrogen content of the specimen and the measurement of the concentration of heavy nitrogen are carried out by separate procedures totally different from each other and, therefore, of are unacceptably time-consuming where the test in question is to be performed on numerous specimens.

SUMMARY OF THE INVENTION

It is, therefore, an object of the present invention to provide a method for determination of the total nitrogen content and the heavy nitrogen concentration of a specimen, irrespective of whether the specimen available is in a relatively small amount or whether the test involves numerous specimens.

It has now been discovered that the determination of total nitrogen content and the determination of heavy nitrogen content in a given specimen can both be accomplished quickly by decomposing the specimen in a sealed tube by the Dumas' method, causing all the gases thus generated, except nitrogen, to be absorbed in an absorbent contained in the sealed tube thereby producing a sealed tube containing nitrogen as substantially the only substance in a gaseous form, placing the sealed tube in one compartment maintained throughout under vacuum, breaking the sealed tube therein and thereby liberating the nitrogen from the interior of the tube into the compartment, measuring the volume and pressure of the liberated nitrogen and determining by calculation the total nitrogen content of the specimen, and thereafter introducing a part of the liberated nitrogen into a separate gas-receiving tube installed within an apparatus in communication with the sample compartment. The gas-receiving tube is there sealed and the heavy nitrogen concentration within the sealed tube is measured by a spectroscopic method or some other conventional method of measurement.

More specifically, the analytical apparatus of the present invention, includes a unit wherein a specimen is sealed in conjunction with copper oxide and calcium oxide in a tube under vacuum to produce a sealed specimen tube; a unit wherein a sealed nitrogen-containing tube, obtained by heating the sealed specimen tube so as to burn the specimen and expel nitrogen, is broken under vacuum to release the nitrogen therefrom and the volume and pressure of the released nitrogen are measured for the purpose of determining the total nitrogen, a unit wherein a part of the released nitrogen is captured in another tube and sealed (the heavy nitrogen concentration in this sealed tube is measured); and a unit which communicates with all the units described above and functions to evacuate their interiors.

BRIEF EXPLANATION OF THE DRAWINGS

In the accompanying drawings;

FIG. 1 is an explanatory diagram illustrating the entire apparatus of the present invention; and FIG. 2 is a diagram illustrating the various stages in the formation of a sealed specimen tube in the apparatus of the present invention.

DETAILED DESCRIPTION OF THE INVENTION

As shown in FIG. 1, the apparatus of the present invention includes a unit (D) wherein a tube 1 containing a specimen obtained from living organisms, (plant or animal) from other inorganic and organic substances, in conjunction with copper oxide and calcium oxide, is sealed in a specimen tube; a unit (A) having a compartment 7 provided with a weight 6 for fracturing, within the evacuated system, a sealed nitrogen-containing sample tube 5, obtained by heating the sealed specimen tube so as to burn the specimen and release nitrogen, and a manometer 14 for measuring the pressure of the released nitrogen for the purpose of determining the total nitrogen present within the tube 5; a unit (B) communicating with unit (A), and having another tube 15 into which a part of the released nitrogen is introduced in order to produce a sealed nitrogen tube for measuring heavy nitrogen concentration and a unit (C) having a device 22 for evacuating the entire system, i.e., units (D), (A) and (B).

In determining the total nitrogen and heavy nitrogen contents of a given specimen by use of this apparatus, the first step is (a) to fuse and close one of the two open ends of a hollow glass tube as by a burner, (b) to place the specimen 23 and copper oxide 24 in the hollow glass tube now having one closed end and provide the tube with a constriction at a proper point by heating by use of a burner and (c) to place glass wool 25 on the constriction formed as described above in the tube and to deposit calcium oxide 26 on the glass wool 25 as illustrated in FIG. 2. The second step is attaching the tube 1 now containing the specimen, copper oxide and calcium oxide to a socket 2 in the unit (D) for formation of the sealed specimen tube illustrated in FIG. 1, closing the cock 20 and opening the cock 21 and the cock 4, then actuating a device 22 designed to evacuate the interior of the system such as a vacuum pump and allowing the interior of the tube 1 to be evacuated until the degree of vacuum, indicated by a vacuum meter 3, falls below the level of $10^{-4}$ mmHg (see step (d) in FIG. 2, for example) and fusing, cutting and closing the tube at a proper point close to the socket 2 as by a burner so as to produce a sealed specimen tube (see step (e) in FIG. 2, for example). The sealed specimen tube obtained as described above is then heated to burn the specimen. The gases generated by the burning of the specimen, to the exclusion of nitrogen, are absorbed by the calcium oxide contained in the tube. A sealed nitrogen-containing tube 5 which now contains nitrogen as the only gaseous substance is thus obtained. In sequent introduction into the unit (A) for determination of total nitrogen shown in FIG. 1, this sealed tube 5 is inserted upwardly into the compartment 7 which is provided with a manometer 14 used for measurement of the pressure of total nitrogen and a weight 6 used for fracturing the sealed tube. To permit the upward insertion of the sealed tube 5, the bottom of the compartment 7 is opened in advance by removing a ground bottom lid 8. In this connection, it is preferable that prior to the insertion of the sealed tube 5, the weight 6, used to fracture the sealed tube 5 and made, for example, of glass containing iron, be inserted, as mounted on top of a glass rod, upwardly from the bottom of the compartment 7 opened by the removal of the bottom lid 8, and raised and hung from the underside of the cock 10. In the insertion of the sealed tube 5 into the compartment 7, it is preferable, for effective fracture of the tube 5, that the tube 5 be introduced with the specimen-containing portion upwards. After the sealed tube 5 which contains nitrogen as the only gaseous substance has been placed in the compartment 7 as described above, the cock 13 and cock 12 in the manometer 14, the cock 11, the cock 18 in unit (B) and cock 20 in unit (C) are opened while the cock 9 for venting to the atmosphere, the cock 17 in unit (B) and cock 21 in the unit (C) are kept closed. Then, the vacuum device 22 is actuated and kept in operation to evacuate the interior of the compartment 7 until the degree of vaccum therein indicated by the vacuum meter 19 falls below $10^{-4}$ mmHg. Thereafter, the cock 13, the cock 11 and the cock 18 are closed and the weight 6 is released to break the sealed tube 5 now containing nitrogen as the sole gaseous substance, with the result that the nitrogen gas is released from the tube 5 interior into the compartment 7. Then, the cock 11 is gradually opened to introduce the released nitrogen gas via the cock 12 into the manometer 14. The pressure of the nitrogen gas causes the heads of right and left oil columns in the manometer 14 to move from their respective zero points. The change in the scale reading is noted. On the basis of the noted change in the scale reading and the ambient temperature measured at the same time, the total nitrogen content can be calculated given the volume of the inner space of the system from the compartment 7 to the zero point on the nitrogen gas side of the manometer 14, the inside diameter of the manometer and the cross-sectional area of the manometer tube. In the next step, the cock 20 in unit (C) is closed, then the cock 17 is opened and thereafter the cock 18 is gradually opened so that a part of the nitrogen released in the unit (A) is let out, up to a degree of vacuum of 3 to 5 mmHg as indicated on the vacuum meter 19, into the unit (B) wherein another tube 15 for receiving the incoming nitrogen is held by a socket 16.

Subsequently, the cock 18 is closed and the tube 15 is fused, cut and sealed as by a burner at a proper point close to the socket 16 to produce a sealed nitrogen tube. The heavy nitrogen concentration in the sealed nitrogen tube thus obtained is measured by an ordinary method such as spectroscopy wherein the sealed nitrogen tube functions as a discharge tube. On the basis of the relation between the value of heavy nitrogen concentration thus found and the value for total nitrogen content determined as described above, the total nitrogen and heavy nitrogen contents of the specimen can be determined by calculation.

According to the present invention, the total nitrogen and heavy nitrogen contents of a given specimen can be determined with extreme ease as described above. The present invention enables a multiplicity of sealed specimen tubes to be prepared at one time by providing additonal sockets 2 and cocks 4 in the unit (D).

EXAMPLE

In the apparatus of the present invention, ears and roots of lowland rice both ground to the form of powder were assayed for total nitrogen and heavy nitrogen contents by following the procedure described above, using in each test run 6 g of copper oxide (powdered product by Kishida Chemical Co., Ltd. for use in elementary analysis) as a combustion reagent, 4 g of calcium oxide (granulated product having a particle diameter of 2 to 8 mm) preheated to the neighborhood of 900° C so as to serve as a gas absorber and 100 mg of the specimen (powdered ears or roots of lowland rice). The results are shown in the following table.

For the purpose of comparison, 500 mg specimens of the same materials were assayed by the Kjeldahl method for total nitrogen and heavy nitrogen contents. The results are also shown in the table. The larger specimen size, 500 mg, was used in the Kjeldahl method, because use of a specimen as small as 100 mg would possibly result in a large error in measurement.

|  | Kjeldahl method | | Method of the present invention | |
| --- | --- | --- | --- | --- |
|  | Total nitrogen% | Heavy nitrogen $^{15}$N (atom)% | Total nitrogen% | Heavy nitrogen $^{15}$N (atom)% |
| Ears | 1.57 | 1.18 | 1.57 | 1.18 |
|  | 1.54 | 1.20 | 1.57 | 1.20 |
|  |  |  | 1.57 | 1.20 |
|  | 1.56 | 1.19 | 1.57 | 1.19 |
| Roots | 1.73 | 1.88 | 1.74 | 1.88 |
|  | 1.78 | 1.86 | 1.74 | 1.89 |
|  |  |  | 1.75 | 1.88 |
|  | 1.75 | 1.87 | 1.74 | 1.88 |

It is clear from the foregoing table that the results obtained by using the apparatus of the present invention and those obtained by the conventional Kjeldahl method are in close agreement.

What is claimed is:

1. A method for determining the total nitrogen content of a given specimen, said method comprising:
   sealing the specimen together with calcium oxide and copper oxide in a container;
   heating the sealed container to a temperature sufficient to cause the specimen to undergo combustion and generate nitrogen;
   opening the sealed container in an evacuated environment to release the generated nitrogen;
   measuring the volume and pressure of the nitrogen thus released.

* * * * *